United States Patent [19]

Frant

[11] Patent Number: 5,300,442
[45] Date of Patent: Apr. 5, 1994

[54] METHOD AND DEVICE FOR MEASURING CHLORINE CONCENTRATIONS WITH ENHANCED SENSITIVITY

[75] Inventor: Martin Frant, Newton, Mass.

[73] Assignee: Orion Research, Inc., Cambridge, Mass.

[21] Appl. No.: 697,880

[22] Filed: May 9, 1991

[51] Int. Cl.$^5$ ................. G01N 27/00; G01N 27/76
[52] U.S. Cl. ......................... 436/125; 436/150; 436/151; 422/68.1; 422/75; 422/82.01; 422/82.02; 204/153.13; 204/400
[58] Field of Search ............. 422/75, 81, 68.1, 82.02, 422/82.03, 82.01; 436/125, 151, 175, 150; 204/153.13, 400, 405

[56] References Cited

U.S. PATENT DOCUMENTS

| | | | |
|---|---|---|---|
| 3,412,199 | 11/1968 | Morrow, Jr. | 204/1 |
| 4,018,563 | 4/1977 | Lundqwist et al. | 23/230 R |
| 4,049,382 | 9/1977 | Ross, Jr. et al. | 23/230 R |
| 4,131,428 | 12/1978 | Diggens | 23/230 R |
| 4,196,056 | 4/1980 | Kumar | 204/1 T |
| 4,270,925 | 6/1981 | Isa et al. | 23/230 R |
| 4,318,884 | 3/1982 | Suzuki | 422/63 |
| 4,318,885 | 3/1982 | Suzuki et al. | 422/68 |
| 4,322,215 | 3/1982 | Huber et al. | 23/230 |
| 4,391,775 | 7/1983 | Huber et al. | 422/68 |
| 4,533,518 | 8/1985 | Hanaoka et al. | 422/70 |
| 4,795,611 | 1/1989 | van der Smissen | 422/56 |
| 4,938,926 | 7/1990 | Reiss | 422/58 |

OTHER PUBLICATIONS

Rochow, "Modern Descriptive Chemistry" W. B. Sanders Co., Philadelphia 1977 pp. 187–188.
Douglas et al. "Concepts and Models of Inorganic Chemistry" John Wiley & Sons, Inc. New York 1983 pp. 627–630.
Windholz, M. ed. "The Merck Index" 10 edition Merck & Co., Inc Rahway, N.J. 1983 p. 1102.
Rochon, "Modern Descriptive Chemistry" W. B. Saunders Co. Philadelphia 1977 pp. 148–150.

*Primary Examiner*—James C. Housel
*Assistant Examiner*—David Redding
*Attorney, Agent, or Firm*—Cesari and McKenna

[57] ABSTRACT

A method and apparatus for measuring the amount of residual chlorine in solution with enhanced accuracy. The basic measurement technique involves introducing a solution of iodide ion into the sample to reduce the chlorine, thereby producing a proportionate amount of iodine; measurement of the iodine concentration is used to infer the initial amount of chlorine. The accuracy of this measurement technique is enhanced by introducing a sufficient amount of scavenger, preferably finely divided zinc metal, into the iodide solution to react with trace amounts iodine present therein.

9 Claims, No Drawings

METHOD AND DEVICE FOR MEASURING CHLORINE CONCENTRATIONS WITH ENHANCED SENSITIVITY

BACKGROUND OF THE INVENTION

A. Field of the Invention

The present invention relates generally to potentiometric measurements, and more particularly to measurement of aqueous chlorine ($Cl_2$) concentrations using electrochemical means.

B. Description of the Related Art

Chlorine is widely used to purify water for drinking and recreation, to remove or neutralize effluents such as cyanides in wastewater, and to cleanse various foods prior to packaging and distribution. In addition, chlorine is often produced as a byproduct in synthetic and other industrial chemical reactions. Whether introduced deliberately or inadvertently into sources of potable water, even relatively minute amounts of residual chlorine can produce deleterious health consequences. For example, recent federal guidelines prohibit certain discharges of wastewater having chlorine concentrations in excess of 50 parts per billion (ppb), or less than $10^{-6}$ M.

Traditionally, aqueous chorine concentrations have been measured using colorimetry, amperometric titration or starch-iodide titration. More recently, potentiometric measurement techniques have been introduced. In one such system, described in U.S. Pat. No. 4,049,382 (the entire disclosure of which is hereby incorporated by reference), a test reagent comprising a dissociated complex of alkali metal ion and iodide ion is first introduced into an acidified sample. The iodide ion is present in sufficient quantity to react with all of the residual chlorine according to the following reaction:

$$Cl_2 + I^- \rightarrow I_2 + Cl^-$$

Since this reaction proceeds to completion, the final concentration of iodine ($I_2$) reflects the initial concentration of chlorine in the sample. The iodine concentration is measured using two electrode elements, one having a noble metal oxidation-reduction element (sensitive to the concentration ratio $[I_2]/[I^-]$) and the other having an iodide-sensitive membrane. These electrodes can be separate devices, or can be combined into a unitary "combination electrode" design.

The well-known Nernst equation describes the electric potential developed by each element. For the noble metal element, the potential $E_{nm}$ is given by:

$$E_{nm} = E_o + (RT/2F) \times \log([I_2]/[I^-]^2)$$
$$= E_o + (RT/2F) \times \log[I_2] - (RT/F) \times \log[I^-]$$

For the iodide-sensitive element, the potential $E_{is}$ is given by:

$$E_{is} = E_o' - (RT/F) \times \log[I^-]$$

Subtracting, $$E_{nm} - E_{is} = E_o'' + (RT/2F) \times \log[I_2]$$

Accordingly, the potential difference between the two electrode elements is proportional to the concentration of iodine and, therefore, to the initial concentration of chlorine in the sample.

Unfortunately, there are inherent limits to the sensitivity of this technique related, we have found, to the age and storage history of the reagents used for measurement. We believe that the culprit is the iodide ion, and have detected a propensity of this species to undergo trace amounts of irreversible oxidation to iodine over time, even at neutral pH. This oxidation, which can be virtually imperceptible, results in the accumulation of iodine in the test reagent before it is used to perform measurements; a test reagent so contaminated produces a distorted measurement of the iodine concentration and, hence, suggests a higher chlorine concentration than actually is the case. Because the degree of iodide oxidation depends on the age of the test reagent as well as various ambient conditions, the amount of excess iodide is wholly unpredictable, eliminating the possibility of calibrating the measurement to account for the excess iodine.

While iodide oxidation does not significantly degrade measurement accuracy in cases of relatively high chlorine concentrations, the effect significantly interferes with measurements involving chlorine levels below 10 ppb.

DESCRIPTION OF THE INVENTION

A. Objects of the Invention

It is, therefore, an object of the present invention to provide a method of overcoming the problem of iodide oxidation in electrochemical measurements of chlorine concentration.

It is another object of the invention to increase the useful life and effectiveness of halogen-based test reagents.

It is a further object of the invention to provide an apparatus for measuring aqueous chlorine concentrations with enhanced sensitivity.

It is yet another object of the invention to extend the storage life of electrochemical reagents.

Other objects will, in part, be obvious and will, in part, appear hereinafter. The invention accordingly comprises an article of manufacture possessing the features and properties exemplified in the constructions described herein and the several steps and the relation of one or more of such steps with respect to the others and the apparatus embodying the features of construction, combination of elements and the arrangement of parts which are adapted to effect such steps, all as exemplified in the following summary and detailed description, and the scope of the invention will be indicated in the claims.

B. Brief Summary of the Invention

The present invention counteracts the oxidation of iodide ion into iodine by introducing a scavenger into the iodide test solution. This scavenger sequesters the iodine from the solution, thereby preventing its interference with measurements. Suitable scavengers remain stable over a long period of time in the iodide test solution (e.g., do not undergo corrosion or interact with the iodide ion), are easily separated from the iodide solution, and fully react with the iodine to produce compounds that either precipitate or are otherwise electrochemically inert with respect to the test electrodes.

Our preferred scavenger is finely divided zinc metal, a small amount of which is placed in the iodide solution and left to settle to the bottom thereof. The zinc reacts with iodine according to the following reaction:

$$Zn + I_2 \rightarrow ZnI_2$$

This reaction proceeds to completion, and the zinc iodide product does not interfere with the reduction of chlorine due to the high oxidation state of zinc.

It has been known to use cadmium in an acidic solution to remove stray iodine from electrochemical test solutions. However, cadmium is highly toxic, and thus unsuited for many applications. Furthermore, we are unaware of any suggestion in the prior art that iodine formation can occur in neutral iodide solutions at levels sufficient to interfere with chlorine measurements, and unaware of any suggestion that scavengers should be used in such solutions to address this problem.

C. Detailed Description of the Invention

The present invention is preferably practiced in the form of a kit that contains a noble-metal electrode, an iodine-sensitive electrode, a standard solution having a known chlorine concentration, an acid solution to promote the reaction with chloride ion, and a solution of potassium iodide. To the latter solution is added a relatively small amount of finely divided zinc, which settles to the bottom of the container. The amount of added zinc is not critical; it must be sufficient to react with the trace amounts of iodine, but preferably not in excess. The morphology and particle size also are not critical, although "mossy" zinc is preferred. The zinc particles are sufficiently fine to present an adequate reactive surface to the solution; surface oxidation can occur if the zinc particles are too small, which also results in reduction of effective surface area and, therefore, their reactive capacities.

The zinc-containing potassium iodide solution is preferably carried in a vessel that is covered with a filter membrane that prevents the passage of the zinc therethrough when the contained solution is poured into the sample; if the zinc enters the sample solution, it will interfere with measurement accuracy by reacting with the very iodine that provides the basis for assessing initial chlorine concentrations.

In operation, the electrodes are connected to a suitable meter or recording device (such as a chart plotter). Small amounts of the acid and potassium-iodide solutions are added to the standard solution, the electrodes immersed therein, and readings taken to calibrate the system. Small amounts of the acid and potassium-iodide solutions are then added to the vessel containing the sample solution and, after the contents of the vessel have had time to react, the now-calibrated electrodes are immersed therein.

Retaining the acid as a separate solution until the time of use helps to reduce the level of iodide oxidation that occurs over time; the added scavenger effectively removes all traces of the iodine that would otherwise interfere with chlorine measurement.

The use of a scavenger such as zinc is useful in other circumstances where halogen oxidation can interfere with electrochemical measurements, such as titration analyses wherein potassium iodide is used as a titrant. In the application described herein, the ability to sequester stray iodine markedly enhances the accuracy of chlorine measurements at low concentrations, and facilitates compliance with increasingly stringent environmental guidelines regarding residual chlorine.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of measuring chlorine concentrations in an aqueous sample solution, comprising the steps of:
   a. preparing a neutral iodide test solution by combining aqueous iodide ion with finely divided zinc metal;
   b. introducing a sufficient amount of the iodide test solution into the sample to reduce any chlorine present in the sample and thereby form a proportionate amount of iodine;
   c. thereafter measuring the amount of iodine present in solution; and
   d. reporting the amount of chlorine initially present in the sample solution based on the measured amount of iodine.

2. The method of claim 1 wherein the amount of zinc added is sufficient to react substantially completely with stray iodine in the iodide test solution.

3. The method of claim 1 further comprising the step of preventing the zinc from combining with the sample.

4. The method of claim 1 further comprising the step of adding acid to the sample to promote reaction with iodide ion.

5. A method of enhancing the electrochemical measurement accuracy of a neutral test solution containing iodide ion, comprising the step of introducing therein a sufficient amount of zinc to react with stray iodine and thereby render it unable to interfere with a desired electrochemical measurement.

6. Apparatus for measuring the concentration of chlorine in an aqueous test solution, comprising:
   a. a neutral iodide test solution containing aqueous iodide ion and finely divided zinc metal;
   b. means for introducing a sufficient amount of the iodide test solution into the sample to reduce any chlorine present in the sample and thereby form a proportionate amount of iodine;
   c. means for measuring the concentration of iodine; and
   d. means coupled to the measuring means for reporting the amount of chlorine initially present in the sample solution based on the measured amount of iodine.

7. The apparatus of claim 6 wherein the amount of zinc in the iodide test solution is sufficient to react substantially completely with stray iodine in the iodide test solution.

8. The apparatus of claim 6 further comprising means for preventing the zinc from combining with the sample.

9. The apparatus of claim 6 further comprising means for adding acid to the sample to promote reaction with iodide ion.

* * * * *